(12) United States Patent
Oki et al.

(10) Patent No.: US 9,138,410 B2
(45) Date of Patent: Sep. 22, 2015

(54) COMPOSITIONS FOR NASAL ADMINISTRATION OF PHARMACEUTICALS

(71) Applicant: Shin Nippon Biomedical Laboratories, LTD., Kagoshima (JP)

(72) Inventors: Toshikazu Oki, Kanagawa (JP); Takashi Hanafusa, Hyogo (JP); Shunji Haruta, Kagoshima (JP)

(73) Assignee: Shin Nippon Biomedical Laboratories, Ltd., Kagoshima (JP)

( * ) Notice: Subject to any disclaimer, the term of this patent is extended or adjusted under 35 U.S.C. 154(b) by 0 days.

(21) Appl. No.: 13/827,859

(22) Filed: Mar. 14, 2013

(65) Prior Publication Data

US 2013/0287852 A1    Oct. 31, 2013

Related U.S. Application Data

(63) Continuation of application No. 12/346,537, filed on Dec. 30, 2008, now Pat. No. 8,435,554, which is a continuation of application No. 10/545,764, filed as application No. PCT/JP03/01948 on Feb. 21, 2003, now Pat. No. 7,638,138.

(51) Int. Cl.
    *A61K 9/14*    (2006.01)
    *A61K 38/00*   (2006.01)
    *A61K 38/24*   (2006.01)
    *A61K 38/29*   (2006.01)
    *A61K 9/00*    (2006.01)
    *A61K 38/22*   (2006.01)
    *A61K 38/23*   (2006.01)
    *A61K 38/26*   (2006.01)
    *A61K 38/27*   (2006.01)
    *A61K 38/28*   (2006.01)

(52) U.S. Cl.
    CPC ............ *A61K 9/14* (2013.01); *A61K 9/0043* (2013.01); *A61K 38/22* (2013.01); *A61K 38/23* (2013.01); *A61K 38/26* (2013.01); *A61K 38/27* (2013.01); *A61K 38/28* (2013.01); *A61K 38/29* (2013.01)

(58) Field of Classification Search
    USPC ......... 424/434, 46, 489, 499; 514/10.3, 11.4, 514/11.7, 11.8, 5.9
    See application file for complete search history.

(56) References Cited

U.S. PATENT DOCUMENTS

| | | |
|---|---|---|
| 3,906,950 A | 9/1975 | Cocozza |
| 4,013,075 A | 3/1977 | Cocozza |
| 4,159,345 A | 6/1979 | Takeo et al. |
| 4,226,233 A | 10/1980 | Kritzer |
| 4,300,545 A | 11/1981 | Goodnow et al. |
| 4,613,500 A | 9/1986 | Suzuki et al. |
| 4,889,114 A | 12/1989 | Kladders |
| 5,098,907 A | 3/1992 | Kondo et al. |
| 5,320,094 A | 6/1994 | Laube et al. |
| 5,419,315 A | 5/1995 | Rubsamen |
| 5,647,349 A | 7/1997 | Ohki et al. |
| 5,672,581 A | 9/1997 | Rubsamen et al. |
| 5,674,507 A * | 10/1997 | Banker et al. .......... 424/401 |
| 5,683,361 A | 11/1997 | Elk et al. |
| 5,731,303 A | 3/1998 | Hsieh |
| 5,756,483 A | 5/1998 | Merkus |
| 5,804,209 A | 9/1998 | De Ponti et al. |
| 5,810,004 A | 9/1998 | Ohki et al. |
| 5,939,100 A | 8/1999 | Albrechtsen et al. |
| 5,942,242 A | 8/1999 | Mizushima et al. |
| 5,948,749 A | 9/1999 | Igarashi et al. |
| 5,958,458 A | 9/1999 | Norling et al. |
| 5,989,217 A | 11/1999 | Ohki et al. |
| 6,136,295 A | 10/2000 | Edwards et al. |
| 6,197,328 B1 | 3/2001 | Yanagawa |
| 6,248,363 B1 | 6/2001 | Patel et al. |
| 6,273,086 B1 | 8/2001 | Ohki et al. |
| 6,298,846 B1 | 10/2001 | Ohki et al. |
| 6,516,795 B1 | 2/2003 | Bougamont et al. |
| 6,815,424 B2 | 11/2004 | Vickery et al. |
| 6,824,080 B2 | 11/2004 | Matsugi et al. |
| 6,835,389 B1 | 12/2004 | Dohi et al. |
| 6,855,913 B2 | 2/2005 | Nikodym |
| 6,906,027 B2 | 6/2005 | Oki et al. |
| 7,022,311 B1 | 4/2006 | Ohkuma et al. |
| 7,115,281 B2 | 10/2006 | Singh et al. |
| 7,278,982 B2 | 10/2007 | Tsutsui |
| 7,306,787 B2 | 12/2007 | Tarara et al. |
| 7,353,823 B2 | 4/2008 | Tsutsui |
| 7,638,138 B2 | 12/2009 | Oki et al. |
| 7,806,117 B2 | 10/2010 | Tsutsui |

(Continued)

FOREIGN PATENT DOCUMENTS

| | | |
|---|---|---|
| EP | 0122036 A1 | 10/1984 |
| EP | 0147755 A2 | 7/1985 |

(Continued)

OTHER PUBLICATIONS

U.S. Appl. No. 12/576,219, filed Oct. 8, 2009, Tsutsui et al.
"Fluorouracil" definition viewed on the National Cancer Institute website at www.cancergov/drugdictionary?cdrid=43130 on May 31, 2012.
European search report and opinion dated Dec. 19, 2011 for Application No. 07860016.0.
European search report dated Jul. 15, 2008 for Application No. 05768543.0.

(Continued)

*Primary Examiner* — Mina Haghighatian
(74) *Attorney, Agent, or Firm* — Wilson, Sonsini, Goodrich & Rosati

(57) ABSTRACT

Compositions for nasal administration, which comprise a pharmaceutical, a physiologically active peptide, or a peptide-related compound, and as the carrier thereof, crystalline cellulose with a specific particle diameter and/or partially pregelatinized starch are provided. Such compositions improve the in vivo absorption efficiency of pharmaceuticals.

18 Claims, 8 Drawing Sheets

(56) References Cited

U.S. PATENT DOCUMENTS

| | | |
|---|---|---|
| 8,062,670 B2 | 11/2011 | Baran, Jr. et al. |
| 8,337,817 B2 | 12/2012 | Nagata et al. |
| 8,435,554 B2 | 5/2013 | Oki et al. |
| 2001/0027301 A1 | 10/2001 | Lau et al. |
| 2001/0038824 A1 | 11/2001 | Horii et al. |
| 2002/0002172 A1 | 1/2002 | Bell-huff et al. |
| 2002/0012688 A1 | 1/2002 | Dohi et al. |
| 2002/0040139 A1 | 4/2002 | Billotte et al. |
| 2002/0062829 A1 | 5/2002 | Ohki et al. |
| 2003/0199424 A1 | 10/2003 | Smith et al. |
| 2004/0063615 A1 | 4/2004 | Oki et al. |
| 2004/0076588 A1 | 4/2004 | Batycky et al. |
| 2004/0092428 A1 | 5/2004 | Chen et al. |
| 2004/0173211 A1 | 9/2004 | Kladders et al. |
| 2004/0241232 A1 | 12/2004 | Brown et al. |
| 2005/0022812 A1 | 2/2005 | Hrkach |
| 2005/0042177 A1 | 2/2005 | Ryde et al. |
| 2005/0118272 A1 | 6/2005 | Besse et al. |
| 2005/0142073 A1 | 6/2005 | Watts et al. |
| 2005/0158250 A1 | 7/2005 | Oki et al. |
| 2005/0177095 A1 | 8/2005 | Tsutsui |
| 2005/0232988 A1 | 10/2005 | Venkatesh et al. |
| 2006/0057213 A1 | 3/2006 | Larhrib et al. |
| 2006/0106057 A1 | 5/2006 | Daniel et al. |
| 2006/0116657 A1 | 6/2006 | Schmid |
| 2006/0216352 A1 | 9/2006 | Nystrom et al. |
| 2006/0217658 A1 | 9/2006 | Tsutsui |
| 2006/0233715 A1 | 10/2006 | Oki et al. |
| 2007/0055200 A1 | 3/2007 | Gilbert |
| 2007/0060868 A1 | 3/2007 | Tsutsui et al. |
| 2007/0065509 A1 | 3/2007 | Kanikanti et al. |
| 2007/0098804 A1 | 5/2007 | Aronhime et al. |
| 2007/0178164 A1 | 8/2007 | Blau |
| 2007/0184109 A1 | 8/2007 | Floyd et al. |
| 2007/0249674 A1 | 10/2007 | Bolton et al. |
| 2007/0272763 A1 | 11/2007 | Dunne et al. |
| 2008/0029084 A1 | 2/2008 | Costantino et al. |
| 2008/0031959 A1 | 2/2008 | Blondino et al. |
| 2008/0090841 A1 | 4/2008 | Johnson et al. |
| 2008/0127972 A1 | 6/2008 | Morton |
| 2008/0260848 A1 | 10/2008 | Nagata et al. |
| 2008/0286362 A1 | 11/2008 | Baran, Jr. et al. |
| 2009/0157037 A1 | 6/2009 | Iyer et al. |
| 2011/0033544 A1 | 2/2011 | Nagata et al. |
| 2011/0045088 A1 | 2/2011 | Tsutsui et al. |
| 2013/0095145 A1 | 4/2013 | Nagata et al. |

FOREIGN PATENT DOCUMENTS

| | | |
|---|---|---|
| EP | 0761248 A1 | 3/1997 |
| EP | 0943326 A1 | 9/1999 |
| EP | 1025859 A1 | 8/2000 |
| EP | 1108423 A1 | 6/2001 |
| EP | 1454648 A1 | 9/2004 |
| EP | 1504780 A1 | 2/2005 |
| EP | 1785145 A1 | 5/2007 |
| GB | 2395900 A | 6/2004 |
| GB | 2448183 A | 10/2008 |
| JP | 3912469 | 7/1964 |
| JP | 53127553 | 11/1978 |
| JP | S 54-20126 A | 2/1979 |
| JP | 54062328 | 5/1979 |
| JP | 59-34267 A | 2/1984 |
| JP | S 59-163313 A | 9/1984 |
| JP | 60-185564 | 9/1985 |
| JP | 60-224616 | 11/1985 |
| JP | 62-42888 | 9/1987 |
| JP | 63267731 | 11/1988 |
| JP | 3-29146 | 3/1991 |
| JP | 5032560 A | 2/1993 |
| JP | 7-165613 A | 6/1995 |
| JP | 8-098888 | 4/1996 |
| JP | H 08-206208 A | 8/1996 |
| JP | 08243164 | 9/1996 |
| JP | 9-276405 | 10/1997 |
| JP | 9-291026 A | 11/1997 |
| JP | 10059841 | 3/1998 |
| JP | 11/216357 | 8/1999 |
| JP | 11-322582 | 11/1999 |
| JP | 2000-229859 A | 8/2000 |
| JP | 2000-239187 | 9/2000 |
| JP | 2001-55323 A | 2/2001 |
| JP | 2002-255795 A | 9/2002 |
| JP | 2003-154006 A | 5/2003 |
| JP | 2003-175103 A | 6/2003 |
| JP | 2003-206227 A | 7/2003 |
| WO | WO 94/04133 A1 | 3/1994 |
| WO | WO 95/12399 A1 | 5/1995 |
| WO | WO 95/34582 A1 | 12/1995 |
| WO | WO 97/31626 A1 | 9/1997 |
| WO | WO 98/30207 A1 | 7/1998 |
| WO | WO 99/16422 A1 | 4/1999 |
| WO | WO 99/16470 A1 | 4/1999 |
| WO | WO 99/51205 A1 | 10/1999 |
| WO | WO 00/12063 | 3/2000 |
| WO | WO 00/12136 A1 | 3/2000 |
| WO | WO 00/23023 A1 | 4/2000 |
| WO | WO 00/38811 A1 | 7/2000 |
| WO | WO 01/26630 A1 | 4/2001 |
| WO | WO 01/32125 A2 | 5/2001 |
| WO | WO 02/32406 A2 | 4/2002 |
| WO | WO 02/094233 A1 | 11/2002 |
| WO | WO 03/004048 | 1/2003 |
| WO | WO 03/030872 A2 | 4/2003 |
| WO | WO 03/077825 A2 | 9/2003 |
| WO | WO 03/095008 A1 | 11/2003 |
| WO | WO 2004/004922 A1 | 1/2004 |
| WO | WO 2005/013937 A2 | 2/2005 |
| WO | WO 2005/056008 A1 | 6/2005 |
| WO | WO 2005/104712 A2 | 11/2005 |
| WO | WO 2006/016530 A1 | 2/2006 |
| WO | WO 2006/040680 A1 | 4/2006 |
| WO | WO 2008/031028 A2 | 3/2008 |
| WO | WO 2008/075102 A1 | 6/2008 |
| WO | WO 2008/078730 A1 | 7/2008 |
| WO | WO 2008/031028 A3 | 11/2008 |
| WO | WO 2009/095684 A1 | 8/2009 |

OTHER PUBLICATIONS

Hens, et al., "BMP4 and PTHrP interact to stimulate ductal outgrowth during embryonic mammary development and to inhibit hair follicle induction," Development 2007, 134, pp. 1221-1230.

Hibberd, et al. Immunization strategies for the immunocompromised host: the need for immunoadjuvants. Ann Intern Med. Jun. 15, 1989;110(12):955-6.

International search report (partial) dated Dec. 21, 2010 for PCT Application No. IB2010/02168.

International search report Jun. 8, 2010 for PCT Application No. JP2010/003285.

International search report and written opinion dated Jun. 28, 2011 for PCT Application No. IB2010/02168.

International search report dated Nov. 1, 2005 for PCT Application No. JP2005/014389.

International search report dated Feb. 5, 2008 for PCT Application No. JP2007/074787.

International search report dated May 7, 2003 for PCT Application No. JP2003/001948.

Ishikawa, et al. Improved nasal bioavailability of elcatonin by insoluble powder formulation. Int J Pharm. Aug. 14, 2001;224(1-2):105-14.

Kleinebudde, et al. Influence of degree of polymerization on behavior of cellulose during homogenization and extrusion/spheronization. AAPS Pharmsci 2000, 2(2) Article 21, 1-10.

Merriam-Webster's Collegiate Dictionary, 10th edition, Merriam-Webster Incorporated: Springfield, Massachusetts, 1993, pp. 41.

Office action dated Jan. 13, 2011 for U.S. Appl. No. 12/346,537.

Office action dated Jan. 20, 2011 for U.S. Appl. No. 12/576,219.

Office action dated Jan. 29, 2008 for U.S. Appl. No. 10/545,764.

Office action dated Mar. 4, 2013 for U.S. Appl. No. 12/848,850.

Office action dated Apr. 12, 2012 for U.S. Appl. No. 12/576,219.

(56) References Cited

OTHER PUBLICATIONS

Office action dated Apr. 20, 2012 for U.S. Appl. No. 12/780,433.
Office action dated May 7, 2013 for U.S. Appl. No. 11/660,131.
Office action dated Jun. 4, 2012 for U.S. Appl. No. 12/521,116.
Office action dated Jun. 10, 2013 for U.S. Appl. No. 12/576,219.
Office action dated Jun. 25, 2012 for U.S. Appl. No. 12/346,537.
Office action dated Sep. 6, 2011 for U.S. Appl. No. 12/346,537.
Office action dated Sep. 6, 2011 for U.S. Appl. No. 12/576,219.
Office action dated Sep. 24, 2008 for U.S. Appl. No. 10/545,764.
Office action dated Sep. 27, 2010 for U.S. Appl. No. 11/660,131.
Office action dated Sep. 28, 2011 for JP Application No. 2006-531575 (in Japanese with English translation).
Office action dated Oct. 10, 2012 for U.S. Appl. No. 12/780,433.
Office action dated Oct. 15, 2012 for U.S. Appl. No. 12/848,850.
Office action dated Oct. 29, 2009 for U.S. Appl. No. 11/660,131.
Office action dated Nov. 1, 2012 for U.S. Appl. No. 11/660,131.
Office action dated Dec. 5, 2011 for U.S. Appl. No. 12/346,537.
Rowe, et al (Eds). Handbook of Pharmaceutical Excipients. Pharmaceutical Press. 2003. p. 108-109.
UK combined office action and search report dated Nov. 10, 2010 for Application No. GB1012959.1.
UK search report dated Sep. 9, 2011 for Application No. GB1012959.1.
Advisory action dated Sep. 13, 2013 for U.S. Appl. No. 12/848,850.
European search report and opinion mailed Dec. 20, 2013 for Application No. 10774745.3.
Office action dated Jan. 6, 2014 for U.S. Appl. No. 12/576,219.
Component definition, Dictionary.com, accessed Apr. 1, 2014, pp. 1-4.
Labiris, et al. Pulmonary drug delivery. Part I: physiological factors affecting therapeutic effectiveness of aerosolized medications. Br J Clin Pharmacol. Dec. 2003;56(6):588-99.
Office action dated Apr. 9, 2014 for U.S. Appl. No. 12/780,433.
Partition Coefficient, Wikipedia, accessed Mar. 31, 2014, pp. 1-8.
Topliss, John. Quantitative Structure-Activity Relationships of Drugs, 1983, pp. 2.
Notice of allowance dated Sep. 24, 2014 for U.S. Appl. No. 12/576,219.
Office action dated Oct. 15, 2014 for U.S. Appl. No. 12/780,433.
Office action dated Nov. 24, 2014 for U.S. Appl. No. 13/649,515.
Notice of allowance dated Apr. 22, 2015 for U.S. Appl. No. 12/780,433.
Office action dated Apr. 2, 2015 for U.S. Appl. No. 13/649,515.

* cited by examiner

COMPOSITIONS FOR NASAL ADMINISTRATION OF PHARMACEUTICALS

TECHNICAL FIELD

The present invention relates to pharmaceutical compositions that are administered via the nasal mucosa in granule form. Specifically, the present invention relates to granular compositions for nasal administration of physiologically active peptides such as insulin, or peptide-related compounds.

BACKGROUND ART

At present, insulin is clinically used as a treatment for diabetes in the form of an injectable formulation, and in most cases, it is self-administered by a comparatively simple subcutaneous injection. However, due to the characteristics of this type of injection formulation, the patient is required to self-administer one to four times a day before meals, for life. This troublesome procedure is one of the many problems associated with the treatment of diabetes. Besides insulin, many pharmaceutical peptides are also administered by injections, and there is an ongoing development of dosage forms for convenient administration.

Formulations for nasal administration, in particular, have been proposed to overcome the difficulties associated with administration. For example, a dosage form of insulin formulation, which uses crystalline cellulose as a base and has 90 wt % of particles in the diameter range of 20 to 150 µm, is described in Examined Published Japanese Patent Application No. (JP-B) Sho 62-42888. Considering that for this formulation, "physiologically active polypeptides are preferably water-soluble for nasal mucosal absorption," the Example of this publication discloses that compositions having 90 wt % or more of particles with a diameter of 75 to 149 µm are obtained by: dissolving insulin in aqueous 0.1 N HCl and freeze-drying; mixing the thus-obtained soluble insulin powder with crystalline cellulose; and sifting.

In comparison with compositions in the above-mentioned JP-B Sho 62-42888, Unexamined Published Japanese Patent Application No. (JP-A) Hei 10-59841 (corresponding to EP-A1-943326) discloses compositions which demonstrate excellent nasal absorption and increased maximum blood concentration with highly hydrophilic pharmaceuticals, highly lipophilic pharmaceuticals, and high molecular weight peptides. According to this publication, the above-described effect can be achieved by actively using a water-absorbing and gel-forming base, such as hydroxypropylcellulose, in combination with a crystalline cellulose aggregate comprising particles with a diameter greater than 150 µm, which is contrary to what JP-B Sho 62-42888 suggests.

However, the present inventors are not aware of any information on the practical application of formulations for nasal administration, in particular, those for nasal administration of polypeptide hormones including insulin as described in these prior arts.

DISCLOSURE OF THE INVENTION

In contrast to what is suggested in the above-described JP-B Sho 62-42888 and JP-A Hei 10-59841, the present inventors discovered that compositions for nasal administration of polypeptide hormones or peptide-related compounds, which are prepared by using a partially pregelatinized starch powder having a specific particle diameter, alone or in combination, with a crystalline cellulose powder having a specific sieving particle diameter distribution of less than 150 µm, unexpectedly increase the absorbability and efficacy of pharmaceuticals significantly, compared to compositions in the prior art.

The present invention is based on this finding.

Accordingly, the present invention provides granular compositions for nasal administration comprising a powdered pharmaceutical and a substantially water-insoluble polysaccharide powder as a carrier thereof, wherein the pharmaceutical is selected from physiologically active peptides with a molecular weight of 30,000 or less, in particular, polypeptide hormones and peptide-related compounds, and more specifically, FK-506; and wherein the water-insoluble polysaccharide is at least one selected from: a crystalline cellulose powder with 85 wt % or more of the particles distributed over a partial or the entire sieving particle diameter range of 20 to 60 µm, and a partially pregelatinized starch powder with a mean particle diameter of 20 to 100 µm. Among such compositions, compositions comprising insulin as a pharmaceutical and only the above-described crystalline cellulose as a water-insoluble polysaccharide are also disclosed by the Applicant in JP-A 2001-204784.

BEST MODE FOR CARRYING OUT THE INVENTION

Figure 1:
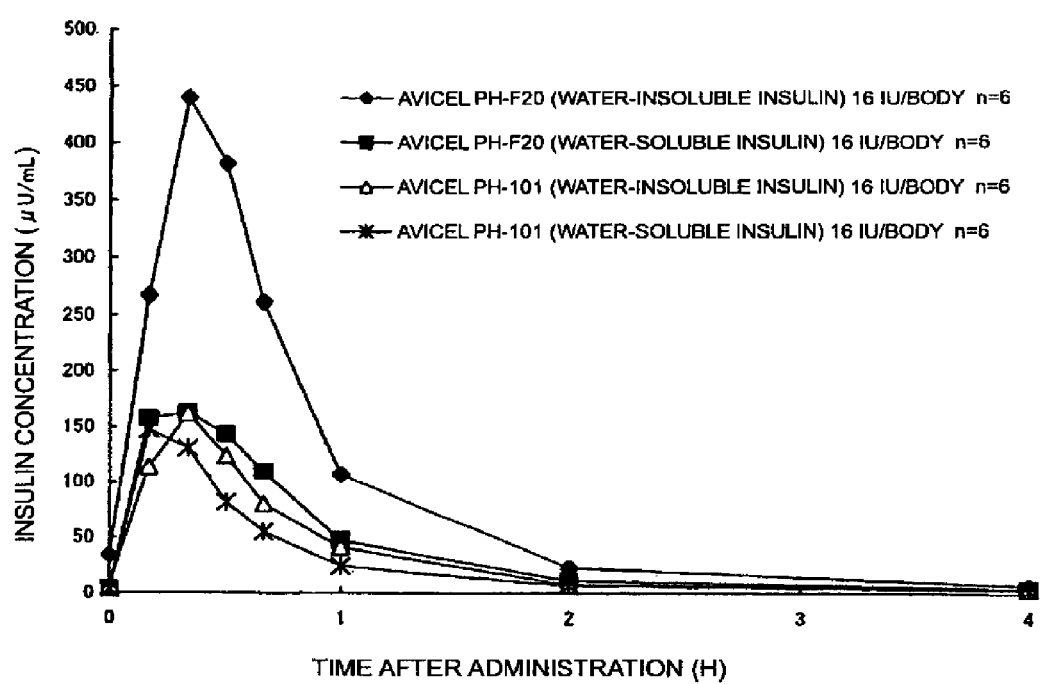
FIG. 1 is a graph showing changes in the serum insulin concentrations after intranasal administration of each composition to cynomolgus monkeys.

Pharmaceuticals of the present invention include physiologically active peptides with a molecular weight of 30,000 or less and peptide-related compounds; in particular, polypeptide hormone compounds and FK-506, that have higher in vivo absorption efficiency than nasal administration and are capable of exerting the efficacy in an effective manner, which are in accordance with the objectives of the present invention.

The physiologically active peptides with a molecular weight of 30,000 or less include linear and cyclic peptides, such as insulin, growth hormone, calcitonin, glucagon, glucagon-like peptide-1 (GLP-1), interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, and cyclosporine. The term "peptide-related compounds" refers to physiologically active substances which comprise at least one peptide bond (amide or imide bond) in the molecular structure, and which are predominantly produced by microorganisms or organisms. A representative example of the peptide-related compounds is FK-506. These pharmaceuticals should not be limited by their origins, preparation methods, or the like. In addition, modified or altered pharmaceuticals can also be used so long as they have the desired efficacy. For example, the term "insulin" includes: human insulin, purified bovine insulin, purified porcine insulin, semi-synthesized human insulin, human iso-insulin, and such, that are currently in clinical use; and all genetically engineered human insulin and insulin modified therefrom, which have an activity equivalent to that of human insulin. Insulin of the present invention is preferably used in powder form. Preferably, the modified insulin powder is only slightly soluble in water or almost insoluble in water (specifically, 1 g of the corresponding insulin powder requires a solvent of 1,000 mL or more and less than 10,000 mL, or 10,000 mL or more to be solved; see, Japanese Pharmacopoeia 13$^{th}$ Edition (Dai 13 Kaisei Nippon Yakkyoku Hou Kaisetu Sho), General Rule A-51). The above-mentioned insulins are slightly soluble or almost insoluble in water, and can be used as an insulin powder of the present invention. Similarly to insulin, other physiologically active peptides and peptide-related compounds that can be used are also not limited; however, the commercially available ones are preferred.

Powdered pharmaceuticals such as the above-described insulin must be a crystalline or non-crystalline fine powder, and must be finer than cellulose particles that constitute a crystalline cellulose powder, or partially pregelatinized starch particles described below. Generally, the surface or the surface microstructure (e.g., pores) of the above-described particles are required to have a particle size that allows the adhesion or inclusion of multiple pharmaceutical powders. Various commercially available pharmaceuticals in bulk powder can be employed directly or after being finely pulverized.

Generally, crystalline cellulose powders (or particles) used in the present invention can be obtained by: obtaining cc-cellulose as pulp from a fibrous plant, partially depolymerizing with an acid, and purifying the water-insoluble fraction. It is possible to use crystalline cellulose powders obtained from rayon filaments or such, as long as they meet the objectives of the present invention. Specifically, crystalline cellulose powders employed in the present invention can be obtained using, for example, the Avicel® series and its modified versions as described in JP-B Sho 39-12469, JP-13 Sho 56-38128, JP-B Sho 61-21201, and JP-B Hei 5-38732, by reducing the particle size using a high-speed impact pulverizer or an air flow-type pulverizer, as necessary; and/or finely pulverizing while increasing the bulk density; and size classifying or sifting to obtain an assembly of particles with the desired particle size.

The crystalline cellulose powder can usually be produced by depolymerization as described above, and its average degree of polymerization is not limited, as long as it meets the objectives of the present invention. A crystalline cellulose powder of the present invention can generally be selected from crystalline cellulose having an average polymerization degree of 15 to 400, preferably 20 to 250, and more preferably 30 to 50. The crystalline cellulose powders of the present invention are not limited, and crystalline cellulose powders that have a bulk density of 0.20 to 0.65 g/cm$^3$, and preferably 0.22 to 0.40 g/cm$^3$ can be utilized. These bulk density values are determined using the Scott Volumeter.

The critical criteria for selecting crystalline cellulose powders of the present invention are the size and distribution pattern of particles which constitute a crystalline cellulose powder. Specifically, it is necessary that approximately 85 wt % or more of the particles are in a partial or the entire sieving particle diameter range of 20 to 60 µm.

Hereinafter, the term "particle diameter" means sieving particle diameter, unless defined otherwise.

The partially pregelatinized starch powder (or particles) used as a second carrier in the present invention can be obtained from any starch using any method of partial pregelatinization, so long as it meets the objectives of the present invention. Without being limited thereto, physically denatured (i.e., heat-denatured) cornstarch is preferred. Such partially pregelatinized starch should be substantially water-insoluble. The term "substantially water-insoluble" means that 5% or less, and preferably 2.5% or less of the content is a water-soluble component at room temperature. The degree of swelling of the "partially pregelatinized" starch measured in pure water at about 20° C. is preferably adjusted to approximately 8 to 9 cm$^3$/g.

Starch which has been size classified into a mean particle diameter of 20 to 100 µm, and preferably about 32 µm or less is used. A representative example of the partially pregelatinized starch, PCS® (degree of swelling: 8 to 9 cm$^3$/g) supplied by Asahi Kasei Corporation, can be employed after the particle size classification, as necessary.

The term "partial or entire range" used to express a particle size distribution of the above-described powders means that in the example of crystalline cellulose, about 85 wt % or more of the crystalline cellulose particles have a particle diameter distribution within the entire range of 20 to 60 µm, or in a partial range thereof, for example, 20 to about 40 µm, 20 to about 55 µm, about 25 to 38 µm, about 25 to 53 µm, or about 38 to 53 µm. Specifically, commercially available Avicel® PH-F20 or PH-M15 can be used after size classification or as it is. Without being limited thereto, the crystalline cellulose powders preferably have a particle diameter distribution of:

10 wt % or fewer particles with a diameter smaller than 25 µm;

20 to 60 wt % particles with a diameter of 25 to 38 µm;

20 to 60 wt % particles with a diameter greater than 38 µm and smaller than or equal to 53 µm; and the remaining particles having a diameter greater than 53 µm (total particles=100 wt %).

According to the present invention, the mixing ratio of powdered insulin, powdered glucagon, powdered calcitonin, parathyroid hormone, gastric inhibitory polypeptide (GIP), C-peptide, cyclosporine, or powdered FK-506, and a crystalline cellulose powder or partially pregelatinized starch, can be adjusted to 1:1 to 1:500 by weight, and more preferably 1:2 to 1:100 by weight.

To prepare compositions of the present invention by homogeneously mixing the above-mentioned powdered insulin with a crystalline cellulose aggregate, a commonly used device (for example, a blender or mixer) for homogeneously mixing a powdered pharmaceutical with a solid carrier can be used. Particles with a diameter smaller than 10 µm or greater than 100 μm may be subsequently removed; however, according to the present inventors' experience, such removal procedures are not needed.

Compositions of the present invention can comprise, in addition to the above-described components, other carriers or base materials, excipients, preservatives, antiseptics, absorption enhancers, or such, as long as they do not contradict the objectives of the present invention. For example, other carriers may include cellulose derivatives described in JP-A Hei 10-59841, such as hydroxypropylcellulose, hydroxypropylmethylcellulose, and methylcellulose. The absorption enhancers include the angelica described in U.S. Pat. No. 5,731,303, which is an essential oil, and its component, cyclopentadecanolide. When other carriers or absorption enhancers like these are used, the resulting compositions are preferably sifted so that more than 80% of the composition particles may have a particle diameter of 70 to 100 μm, preferably 20 to 60 μm.

Hereinbelow, the present invention will be specifically described with reference to examples of compositions for nasal absorption of physiologically active peptides according to the present invention, but it is not to be construed as being limited thereto. In the Examples, the compositions for nasal absorption were nasally administered in a single dose to cynomolgus monkeys (3 to 7 kg weight). Administration was conducted according to a method to administer each capsulated composition into the nasal cavity using an intranasal administration device (Jetlizer, Unisia Jecs Corporation).

Example 1

Pharmacokinetics and Pharmacological Studies of Insulin in Cynomolgus Monkeys

Compositions for nasal absorption were prepared by thoroughly mixing in a mortar, 35 mg (insulin as originally provided) of a water-insoluble insulin powder (Intergen Company, 28.7 IU/mg) and 965 mg of crystalline cellulose (Avicel® PH-101 or Avicel® PH-F20, Asahi Kasei Corporation). Water-soluble insulin was prepared by dissolving 100 mg of a water-insoluble insulin powder in 1 mL of 0.1 N HCl, adding 40 mL of purified water thereto, and freeze-drying the resulting insulin solution. 36 mg of the water-soluble insulin powder (27.7 IU/mg) thus obtained was then mixed with 964 mg of the above-mentioned crystalline cellulose in a mortar to prepare compositions for nasal absorption. Each of the compositions for nasal absorption was administered nasally to cynomolgus monkeys (n=6), and then serum insulin and glucose concentrations were measured.

The serum insulin and glucose concentrations were measured using the EIA method (enzyme immunoassay) and the Glck·G-6-PDH method, respectively.

Pharmacokinetic parameters (mean±standard deviation) obtained using the serum insulin concentrations are shown in Table 1.

Figure 2:
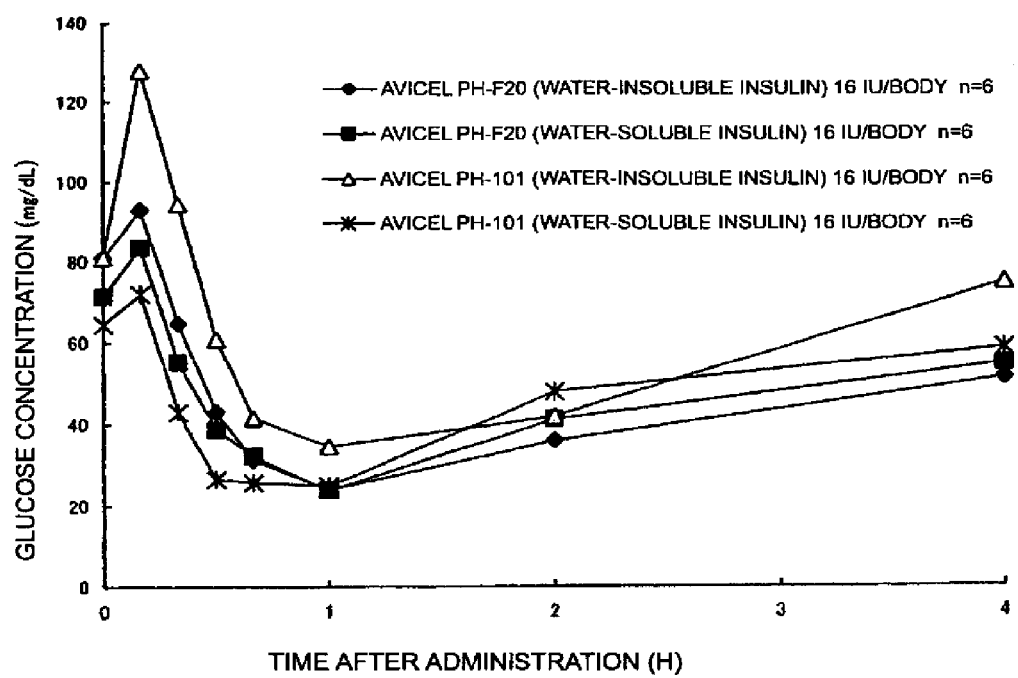
FIG. 2 is a graph showing changes in the serum glucose concentrations after intranasal administration of each composition to cynomolgus monkeys.

For each of the above-described compositions for nasal absorption, the time-course changes in serum insulin and glucose concentrations are shown in FIGS. 1 and 2, respectively. Raw data for FIG. 1 are shown in Tables 2 to 5.

TABLE 1

| Composition | Dose (IU/body) | Number of animals | $C_{max}$ (μU/mL) | $T_{max}$ (h) | $T_{1/2}$ (h) | $AUC_{0-4}$ (μU·h/mL) |
|---|---|---|---|---|---|---|
| Avicel PH-F20 (Water-insoluble insulin) | 16 | 6 | 449.35 ± 183.66 | 0.33 ± 0.10 | 0.75 ± 0.33 | 361.55 ± 167.55 |
| Avicel PH-F20 (Water-soluble insulin) | 16 | 6 | 176.45 ± 143.46 | 0.28 ± 0.13 | 0.86 ± 0.44 | 157.33 ± 138.12 |
| Avicel PH-101 (Water-insoluble insulin) | 16 | 6 | 164.73 ± 70.76 | 0.33 ± 0.10 | 0.78 ± 0.26 | 129.78 ± 78.45 |
| Avicel PH-101 (Water-soluble insulin) | 16 | 6 | 153.95 ± 31.96 | 0.20 ± 0.07 | 0.96 ± 0.79 | 102.88 ± 24.16 |

Note:
$C_{max}$: Maximum blood insulin concentration
$T_{max}$: Time to reach maximum blood concentration
$T_{1/2}$: Time to reduce the maximum blood concentration by half
$AUC_{0-4}$: Total area under the blood concentration curve from 0 to 4 hours

TABLE 2

Administration of Avicel PH-F20 (water-insoluble insulin)
(Time-course changes in insulin concentrations)

| Animal No. | Insulin (μU/mL) | | | | | | | |
|---|---|---|---|---|---|---|---|---|
| | 0 | 10 min | 20 min | 30 min | 40 min | 1 hr | 2 hr | 4 hr |
| 1 | 60.8 | 225.2 | 239.6 | 194.6 | 149.8 | 66.9 | 10.0 | 2.3 |
| 2 | 24.1 | 349.0 | 632.0 | 529.5 | 412.5 | 181.2 | 45.4 | 15.9 |
| 3 | 18.8 | 220.3 | 708.0 | 663.0 | 471.5 | 201.4 | 35.6 | 3.5 |
| 4 | 2.9 | 124.4 | 274.5 | 307.0 | 224.0 | 61.4 | 16.6 | 5.4 |
| 5 | 76.1 | 287.0 | 413.5 | 384.5 | 214.0 | 105.5 | 20.8 | 6.4 |
| 6 | 20.4 | 396.0 | 370.0 | 211.0 | 95.9 | 24.9 | 9.2 | 4.8 |
| Average | 33.85 | 266.98 | 439.60 | 381.60 | 261.28 | 106.88 | 22.93 | 6.38 |
| Standard deviation | 28.18 | 98.01 | 190.70 | 184.77 | 148.64 | 70.49 | 14.60 | 4.88 |

TABLE 3

Administration of Avicel PH-F20 (water-soluble insulin)
(Time-course changes in insulin concentrations)

| | Insulin (µU/mL) | | | | | | | |
|---|---|---|---|---|---|---|---|---|
| Animal No. | 0 | 10 min | 20 min | 30 min | 40 min | 1 hr | 2 hr | 4 hr |
| 1 | 3.8 | 385.0 | 434.0 | 392.0 | 322.0 | 123.2 | 18.4 | 2.3 |
| 2 | 7.0 | 72.6 | 58.6 | 32.2 | 28.5 | 14.0 | 5.7 | 6.7 |
| 3 | 3.4 | 71.4 | 98.2 | 116.3 | 85.7 | 29.4 | 11.3 | 1.3 |
| 4 | 3.2 | 51.2 | 32.0 | 18.4 | 10.8 | 5.6 | 3.0 | 7.9 |
| 5 | 2.8 | 228.1 | 247.0 | 235.6 | 171.8 | 92.4 | 14.6 | 4.8 |
| 6 | 2.7 | 137.6 | 108.0 | 65.7 | 37.9 | 19.1 | 14.0 | 1.3 |
| Average | 3.82 | 157.65 | 162.97 | 143.37 | 109.45 | 47.28 | 11.17 | 4.05 |
| Standard deviation | 1.61 | 128.89 | 152.17 | 144.96 | 119.19 | 48.49 | 5.81 | 2.85 |

TABLE 4

Administration of Avicel PH-101 (water-insoluble insulin)
(Time-course changes in insulin concentrations)

| | Insulin (µU/mL) | | | | | | | |
|---|---|---|---|---|---|---|---|---|
| Animal No. | 0 | 10 min | 20 min | 30 min | 40 min | 1 hr | 2 hr | 4 hr |
| 1 | 8.2 | 80.4 | 63.9 | 32.0 | 19.4 | 8.8 | 3.4 | 3.3 |
| 2 | 5.2 | 83.0 | 162.8 | 125.6 | 96.2 | 44.7 | 9.7 | 2.7 |
| 3 | 12.7 | 159.6 | 265.0 | 265.5 | 211.4 | 103.0 | 16.8 | 5.1 |
| 4 | 2.7 | 113.1 | 182.2 | 160.3 | 73.5 | 41.0 | 4.8 | 3.2 |
| 5 | 4.5 | 62.6 | 89.8 | 40.8 | 23.8 | 13.1 | 5.1 | 3.3 |
| 6 | 5.4 | 184.7 | 207.7 | 120.2 | 56.5 | 35.7 | 5.6 | 5.5 |
| Average | 6.45 | 113.90 | 161.90 | 124.07 | 80.13 | 41.05 | 7.57 | 3.85 |
| Standard deviation | 3.54 | 48.60 | 74.76 | 85.72 | 70.65 | 33.77 | 5.00 | 1.15 |

TABLE 5

Administration of Avicel PH-101 (water-soluble insulin)
(Time-course changes in insulin concentrations)

| | Insulin (µU/mL) | | | | | | | |
|---|---|---|---|---|---|---|---|---|
| Animal No. | 0 | 10 min | 20 min | 30 min | 40 min | 1 hr | 2 hr | 4 hr |
| 1 | 0.4 | 176.6 | 172.3 | 88.0 | 58.7 | 32.6 | 10.9 | 3.6 |
| 2 | 2.0 | 127.9 | 118.3 | 73.2 | 52.3 | 21.4 | 4.2 | 1.4 |
| 3 | 1.8 | 123.2 | 160.2 | 110.3 | 109.2 | 42.7 | 6.7 | 0.6 |
| 4 | 8.6 | 153.4 | 151.6 | 76.2 | 35.9 | 16.1 | 2.0 | 2.2 |
| 5 | 6.0 | 108.8 | 71.9 | 69.0 | 35.5 | 17.3 | 5.0 | 1.9 |
| 6 | 0.9 | 196.8 | 111.5 | 73.5 | 38.5 | 17.6 | 9.4 | 7.2 |
| Average | 3.28 | 147.78 | 130.97 | 81.70 | 55.02 | 24.62 | 6.37 | 2.82 |
| Standard deviation | 3.27 | 34.01 | 37.46 | 15.42 | 28.20 | 10.74 | 3.33 | 2.37 |

Table 1 shows that when 16 IU/body of insulin was intranasally administered, water-insoluble insulin revealed the greatest insulin absorbability with Avicel® PH-F20, followed by water-soluble insulin with Avicel® PH-F20, water-insoluble insulin with Avicel® PH-101, and water-soluble insulin with Avicel® PH-101. In other words, compositions of water-insoluble insulin plus Avicel® PH-F20, water-insoluble insulin plus Avicel® PH-101, and water-soluble insulin plus Avicel® PH-F20, were found to achieve higher insulin absorbability than the water-soluble insulin plus Avicel® PH-101 composition.

Example 2

Pharmacokinetics of Human Growth Hormone in Cynomolgus Monkeys

Compositions for nasal administration were prepared by thoroughly mixing in a mortar, 17.5 mg of powdered human growth hormone (comprising 14.3% human growth hormone; Wako Pure Chemical Industries, Ltd.) and 62.5 mg of crystalline cellulose (Avicel® PH-F20; Asahi Kasei Corporation). The control composition for nasal administration, which comprises crystalline cellulose (Avicel® PH-101; Asahi Kasei Corporation) as a carrier, was also prepared in the same manner. Either of the compositions was nasally administered in a single dose to cynomolgus monkeys (n=3), and then the serum concentrations of human growth hormone were measured.

The human growth hormone concentrations were measured using the EIA method (enzyme immunoassay).

Pharmacokinetic parameters (mean±standard deviation) obtained using the human growth hormone concentrations (the initial value is subtracted) are shown in Table 6.

Figure 3:
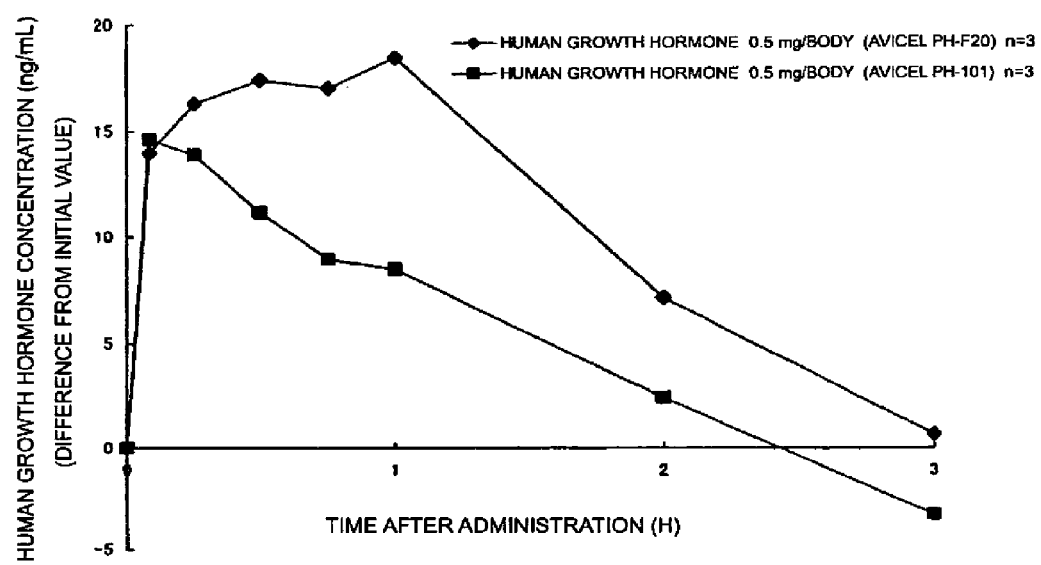
FIG. 3 is a graph showing changes in the serum human growth hormone concentrations (the initial value is subtracted) after intranasal administration of each composition to cynomolgus monkeys.

Time-course changes in the human growth hormone concentrations (the initial value is subtracted) are shown in FIG. 3. Raw data for FIG. 3 are shown in Tables 7 and 8 (Pharmacokinetic parameters have the same meanings as in Table 1).

An insulin composition (hereinafter in-PCS) was prepared by thoroughly mixing in a mortar, 35 mg of water-insoluble insulin powder (Intergen Company; 28.7 IU/mg) (insulin as originally provided) and 965 mg of partially pregelatinized starch (PCS®, Asahi Kasei Corporation) as a carrier, which has been size classified into 32 μm or less (hereinafter s-PCS).

A second composition (hereinafter in-PCS+F20 (1:1)) was prepared by: thoroughly mixing in a mortar, 35 mg of water-insoluble insulin powder (Intergen Company; 28.7 IU/mg) (insulin as originally provided) and 965 mg of crystalline cellulose (Avicel® PH-F20, Asahi Kasei Corporation), to prepare an insulin composition (hereinafter F20); and then mixing in-PCS with F20 at a ratio of 1:1.

TABLE 6

| Composition | Dose (mg/body) | Number of animals | $C_{max}$ (ng/mL) | $T_{max}$ (h) | $T_{1/2}$ (h) | $AUC_{0.3}$ (ng · h/mL) |
|---|---|---|---|---|---|---|
| Human growth hormone (Avicel PH-F20) | 0.5 | 3 | 18.97 ± 6.60 | 0.75 ± 0.43 | 0.56 ± 0.24 | 32.00 ± 13.02 |
| Human growth hormone (Avicel PH-101) | 0.5 | 3 | 14.90 ± 10.05 | 0.19 ± 0.10 | 0.90 ± 0.85 | 18.03 ± 17.54 |

TABLE 7

Administration of human growth hormone (Avicel PH-F20)
(Time-course changes in human growth hormone concentrations)

| | Human growth hormone (ng/mL) (the initial value is subtracted) | | | | | | |
|---|---|---|---|---|---|---|---|
| Animal No. | 0 | 5 min | 15 min | 30 min | 45 min | 1 hr | 2 hr | 3 hr |
| 1 | 0.0 | 3.2 | 5.8 | 9.1 | 8.9 | 11.5 | 5.6 | 0.1 |
| 2 | 0.0 | 19.1 | 21.4 | 20.0 | 18.9 | 19.9 | 6.1 | 1.4 |
| 3 | 0.0 | 19.6 | 21.8 | 23.2 | 23.4 | 24.0 | 9.7 | 3.3 |
| Average | 0.00 | 13.97 | 16.33 | 17.43 | 17.07 | 18.47 | 7.13 | 0.67 |
| Standard deviation | 0.00 | 9.33 | 9.12 | 7.39 | 7.42 | 6.37 | 2.24 | 2.40 |

TABLE 8

Administration of human growth hormone (Avicel PH-101)
(Time-course changes in human growth hormone concentrations)

| | Human growth hormone (ng/mL) (the initial value is subtracted) | | | | | | |
|---|---|---|---|---|---|---|---|
| Animal No. | 0 | 5 min | 15 min | 30 min | 45 min | 1 hr | 2 hr | 3 hr |
| 1 | 0.0 | 8.6 | 9.2 | 7.5 | 7.2 | 9.0 | 4.4 | 7.4 |
| 2 | 0.0 | 26.3 | 26.5 | 24.7 | 21.1 | 16.9 | 5.0 | 2.5 |
| 3 | 0.0 | 9.0 | 6.0 | 1.3 | 1.5 | 0.5 | 2.1 | 4.9 |
| Average | 0.00 | 14.63 | 13.90 | 11.17 | 8.98 | 8.47 | 2.43 | 3.27 |
| Standard deviation | 0.00 | 10.11 | 11.03 | 12.12 | 11.40 | 8.71 | 3.94 | 5.15 |

In Table 6, the human growth hormone compositions for nasal administration comprising Avicel® PH-F20 as a carrier showed an absorbability clearly higher than using Avicel® PH-101 as a carrier (see also FIG. 3).

Example 3

Studies of Pharmacological Effects of Insulin in Cynomolgus Monkeys Using Pregelatinized Starch as a Carrier or an Additive The composition (hereinafter F20) comprising Avicel® PH-F20 as a carrier was compared to the following compositions, using a water-insoluble insulin powder (Intergen Company; 28.7 IU/mg).

Additional compositions were prepared by adding 1% or 10% s-PCS to F20 (hereinafter, F20+1% s-PCS and F20+10% s-PCS).

Each of these compositions was nasally administered to cynomolgus monkeys (n=3 to 6) at 16 IU insulin per body. Serum insulin and glucose concentrations were measured following the administration of each composition.

Insulin and glucose concentrations were measured using the EIA method (enzyme immunoassay) and the Glck·G-6-PDH method, respectively.

Table 9 shows pharmacokinetic parameters (mean±standard deviation) obtained using the serum insulin concentrations, and pharmacological parameters obtained using the serum glucose concentrations.

Figure 4:
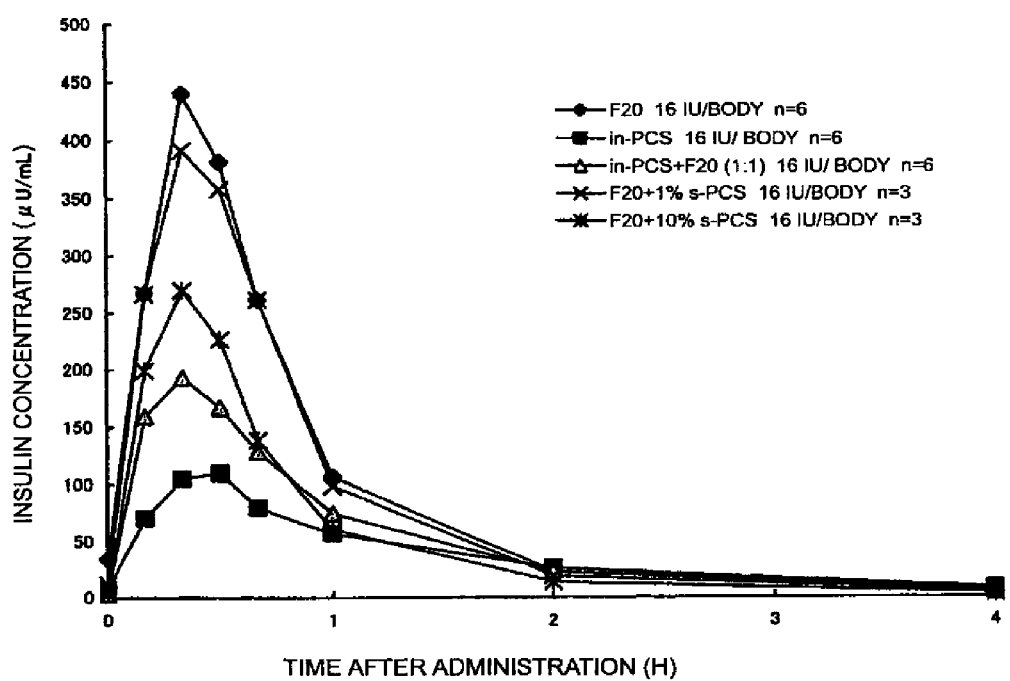
FIG. 4 is a graph showing changes in the serum insulin concentrations after intranasal administration of each composition to cynomolgus monkeys.
Figure 5:
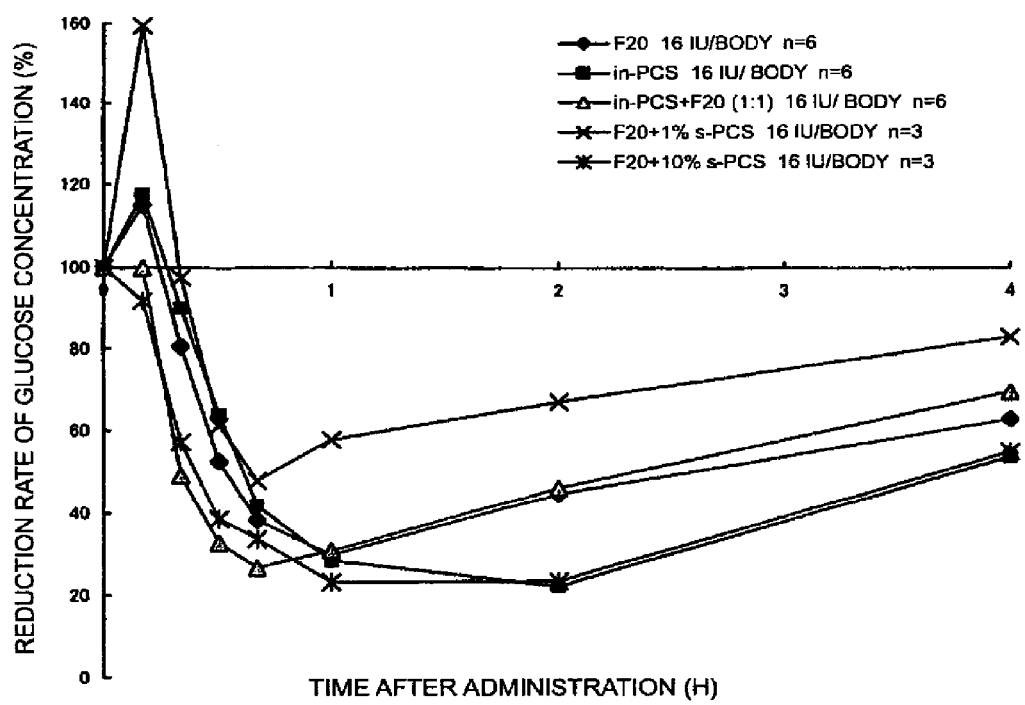
FIG. 5 is a graph showing changes in the rate of reduction (%) in serum glucose concentrations after intranasal administration of each composition to cynomolgus monkeys.

FIGS. 4 and 5 show, respectively, changes in the serum insulin concentrations and the rate of reduction (%) of the serum glucose concentrations over time, using the above-described compositions for nasal absorption. Raw data for FIG. 5 are shown in Tables 10 to 14.

TABLE 9

| Composition | F20 | in-PCS | in-PCS + F20 (1:1) | F20 + 1% s-PCS | F20 + 10% s-PCS |
|---|---|---|---|---|---|
| Administration route | Nasal | Nasal | Nasal | Nasal | Nasal |
| Number of animals | 6 | 6 | 6 | 3 | 3 |
| Dose (IU/body) | 16 | 16 | 16 | 16 | 16 |
| $C_{max}$ (µU/mL) | 449.35 ± 183.66 | 120.63 ± 34.59 | 210.02 ± 60.05 | 402.33 ± 185.28 | 269.97 ± 168.02 |
| $T_{max}$ (h) | 0.33 ± 0.10 | 0.44 ± 0.09 | 0.31 ± 0.12 | 0.39 ± 0.10 | 0.33 ± 0.00 |
| $T_{1/2}$ (h) | 0.75 ± 0.33 | 0.98 ± 0.20 | 0.70 ± 0.24 | 0.61 ± 0.13 | 0.65 ± 0.21 |
| $AUC_{0.4}$ (µU·h/mL) | 361.55 ± 167.55 | 152.17 ± 59.27 | 207.26 ± 119.42 | 334.21 ± 146.05 | 214.89 ± 102.36 |
| $AAC_{0.4}$ (%·h) | 193.25 ± 69.31 | 236.89 ± 48.97 | 195.89 ± 104.79 | 119.21 ± 102.50 | 248.33 ± 26.57 |
| $AAC_{0.4}/AUC_{0.4}$ | 0.5 | 1.6 | 0.9 | 0.4 | 1.2 |

TABLE 10

Administration of F20 (Time-course changes in glucose concentrations)

| Animal No. | Glucose (mg/dL) | | | | | | | |
|---|---|---|---|---|---|---|---|---|
| | 0 | 10 min | 20 min | 30 min | 40 min | 1 hr | 2 hr | 4 hr |
| 1 | 85.07 | 77.95 | 53.43 | 44.40 | 19.23 | 13.26 | 36.26 | 50.58 |
| 2 | 96.47 | 117.31 | 77.69 | 68.04 | 57.48 | 24.21 | 17.95 | 40.33 |
| 3 | 80.62 | 105.72 | 64.02 | 31.01 | 18.51 | 21.54 | 34.60 | 44.29 |
| 4 | 68.43 | 87.74 | 66.95 | 33.74 | 28.02 | 16.26 | 13.87 | 14.10 |
| 5 | 77.97 | 93.67 | 68.23 | 47.85 | 33.50 | 31.68 | 56.55 | 73.31 |
| 6 | 76.74 | 75.08 | 57.93 | 33.13 | 31.89 | 36.97 | 55.52 | 72.92 |
| Average | 80.88 | 92.91 | 64.71 | 43.03 | 31.44 | 23.99 | 35.79 | 50.92 |
| Standard deviation | 9.39 | 16.30 | 8.43 | 14.00 | 14.22 | 9.04 | 18.00 | 22.76 |
| Reduction (%) Mean | 100.00 | 115.09 | 80.60 | 52.51 | 38.44 | 29.99 | 44.88 | 62.93 |
| standard deviation | 0.00 | 16.41 | 11.74 | 11.82 | 13.96 | 12.04 | 23.76 | 29.55 |

TABLE 11

Administration of in-PCS (Time-course changes in glucose concentration)

| Animal No. | Glucose (mg/dL) | | | | | | | |
|---|---|---|---|---|---|---|---|---|
| | 0 | 10 min | 20 min | 30 min | 40 min | 1 hr | 2 hr | 4 hr |
| 1 | 90.40 | 165.10 | 157.59 | 123.66 | 82.02 | 45.60 | 32.53 | 44.50 |
| 2 | 112.71 | 126.08 | 103.15 | 96.35 | 85.86 | 56.69 | 27.61 | 54.72 |
| 3 | 106.98 | 148.35 | 75.27 | 32.50 | 10.67 | 15.25 | 23.91 | 108.31 |
| 4 | 101.65 | 116.66 | 95.01 | 67.87 | 41.65 | 17.60 | 16.67 | 42.53 |
| 5 | 108.78 | 112.18 | 89.90 | 51.98 | 20.33 | 24.83 | 27.01 | 63.03 |
| 6 | 119.28 | 65.52 | 32.44 | 20.28 | 18.26 | 19.11 | 12.56 | 28.89 |
| Average | 106.63 | 122.32 | 92.23 | 65.44 | 43.13 | 29.85 | 23.38 | 57.00 |
| Standard deviation | 9.90 | 34.30 | 40.66 | 39.13 | 33.26 | 17.16 | 7.45 | 27.68 |
| Reduction (%) Mean | 100.00 | 117.66 | 89.92 | 64.03 | 41.98 | 28.53 | 22.43 | 53.84 |
| standard deviation | 0.00 | 42.07 | 47.98 | 43.29 | 34.13 | 17.16 | 8.62 | 25.82 |

TABLE 12

Administration of in-PCS + F20 (1:1) (Time-course changes in glucose concentration)

| Animal No. | Glucose (mg/dL) | | | | | | | |
|---|---|---|---|---|---|---|---|---|
| | 0 | 10 min | 20 min | 30 min | 40 min | 1 hr | 2 hr | 4 hr |
| 1 | 57.70 | 48.72 | 17.64 | 21.62 | 13.59 | 23.72 | 33.70 | 53.75 |
| 2 | 113.51 | 114.41 | 51.53 | 10.60 | 18.88 | 10.35 | 6.25 | 23.43 |
| 3 | 98.94 | 91.61 | 42.72 | 16.58 | 10.46 | 7.61 | 8.64 | 27.58 |

TABLE 12-continued

Administration of in-PCS + F20 (1:1) (Time-course changes in glucose concentration)

| Animal No. | Glucose (mg/dL) | | | | | | | |
|---|---|---|---|---|---|---|---|---|
| | 0 | 10 min | 20 min | 30 min | 40 min | 1 hr | 2 hr | 4 hr |
| 4 | 68.39 | 78.29 | 54.11 | 33.32 | 23.81 | 20.65 | 34.66 | 56.91 |
| 5 | 64.47 | 58.15 | 22.80 | 15.99 | 12.87 | 18.95 | 39.38 | 63.00 |
| 6 | 65.82 | 76.47 | 40.22 | 39.50 | 36.38 | 44.95 | 61.37 | 62.54 |
| Average | 78.14 | 77.94 | 38.17 | 22.94 | 19.33 | 21.04 | 30.67 | 47.87 |
| Standard deviation | 22.52 | 23.51 | 14.93 | 11.18 | 9.64 | 13.25 | 20.62 | 17.72 |
| Reduction (%) | | | | | | | | |
| Mean | 100.00 | 99.78 | 49.12 | 32.85 | 26.80 | 30.97 | 46.27 | 69.60 |
| standard deviation | 0.00 | 13.15 | 18.03 | 19.43 | 16.12 | 22.44 | 33.65 | 35.54 |

TABLE 13

Administration of F20 + 1% s-PCS (Time-course changes in glucose concentration)

| Animal No. | Glucose (mg/dL) | | | | | | | |
|---|---|---|---|---|---|---|---|---|
| | 0 | 10 min | 20 min | 30 min | 40 min | 1 hr | 2 hr | 4 hr |
| 1 | 60.76 | 86.82 | 59.55 | 42.98 | 36.05 | 47.83 | 43.82 | 53.42 |
| 2 | 87.43 | 120.23 | 53.89 | 36.08 | 25.08 | 26.81 | 20.35 | 52.92 |
| 3 | 61.10 | 120.83 | 81.10 | 44.00 | 34.30 | 39.34 | 64.89 | 61.57 |
| Average | 69.76 | 109.29 | 64.85 | 41.02 | 31.81 | 37.99 | 43.02 | 55.97 |
| Standard deviation | 15.30 | 19.46 | 14.36 | 4.31 | 5.89 | 10.57 | 22.28 | 4.86 |
| Reduction (%) | | | | | | | | |
| Mean | 100.00 | 159.39 | 97.46 | 61.34 | 48.05 | 57.92 | 67.20 | 83.07 |
| standard deviation | 0.00 | 33.34 | 35.55 | 17.39 | 16.84 | 24.67 | 41.68 | 20.55 |

TABLE 14

Administration of F20 + 10% s-PCS (Time-course changes in glucose concentrations)

| Animal No. | Glucose (mg/dL) | | | | | | | |
|---|---|---|---|---|---|---|---|---|
| | 0 | 10 min | 20 min | 30 min | 40 min | 1 hr | 2 hr | 4 hr |
| 1 | 74.20 | 42.87 | 28.71 | 20.50 | 22.62 | 20.57 | 16.10 | 38.09 |
| 2 | 94.62 | 136.76 | 94.11 | 63.94 | 51.20 | 35.04 | 21.33 | 54.25 |
| 3 | 113.47 | 82.83 | 38.09 | 23.77 | 19.26 | 6.19 | 30.21 | 64.00 |
| Average | 94.10 | 87.49 | 53.64 | 36.07 | 31.03 | 20.60 | 22.55 | 52.11 |
| Standard deviation | 19.64 | 47.12 | 35.36 | 24.17 | 17.55 | 14.43 | 7.13 | 13.09 |
| Reduction (%) | | | | | | | | |
| Mean | 100.00 | 91.77 | 57.24 | 38.72 | 33.86 | 23.40 | 23.62 | 55.02 |
| standard deviation | 0.00 | 46.33 | 36.65 | 25.22 | 18.80 | 16.22 | 2.63 | 3.23 |

As shown in Table 9, in-PCS, in-PCS+F20 (1:1), and F20+ 10% s-PCS have $AAC_{0.4}/AUC_{0.4}$ values between 0.9 and 1.6, which are significantly higher than that of F20 (0.5), suggesting that compositions using PCS as a carrier or an additive can reduce blood glucose more efficiently, but have lower insulin absorbability than compositions using F20 as a carrier (see also FIGS. 4 and 5).

Examples 4 to 6

Pharmacokinetics Studies of Glucagon, Salmon Calcitonin, and Parathyroid Hormone in Cynomolgus Monkeys Compositions for nasal administration were prepared by thoroughly mixing in a mortar, crystalline cellulose (Asahi Kasei, Corporation; Avicel® PH-F20) and as a physiologically active peptide, 0.6 mg of glucagon (derived from swine; Bachem), 100 IU of salmon calcitonin (Bachem), or 30 µg of parathyroid hormone (1-34, Penisula Laboratories Inc.), for every 16 mg of the composition. The control composition for nasal administration was prepared using crystalline cellulose (Asahi Kasei Corporation; Avicel® PH-101) as a carrier in the same manner. Each of the above-described compositions was nasally administered in a single dose to a cynomolgus monkey (n=1), and then the concentrations of glucagon, salmon calcitonin, and parathyroid hormone in blood were measured.

The blood concentrations of glucagon, salmon calcitonin, and parathyroid hormone were measured using the RIA double antibody method.

Figure 6:
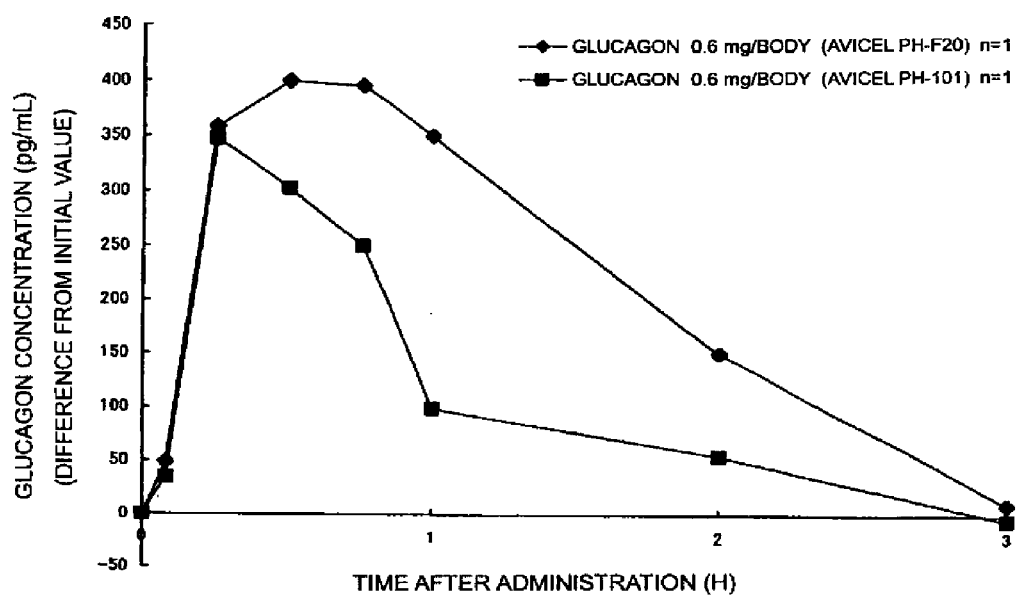
FIG. 6 is a graph showing changes in the blood pharmaceutical concentrations after intranasal administration of each glucagon-comprising composition to cynomolgus monkeys.
Figure 7:
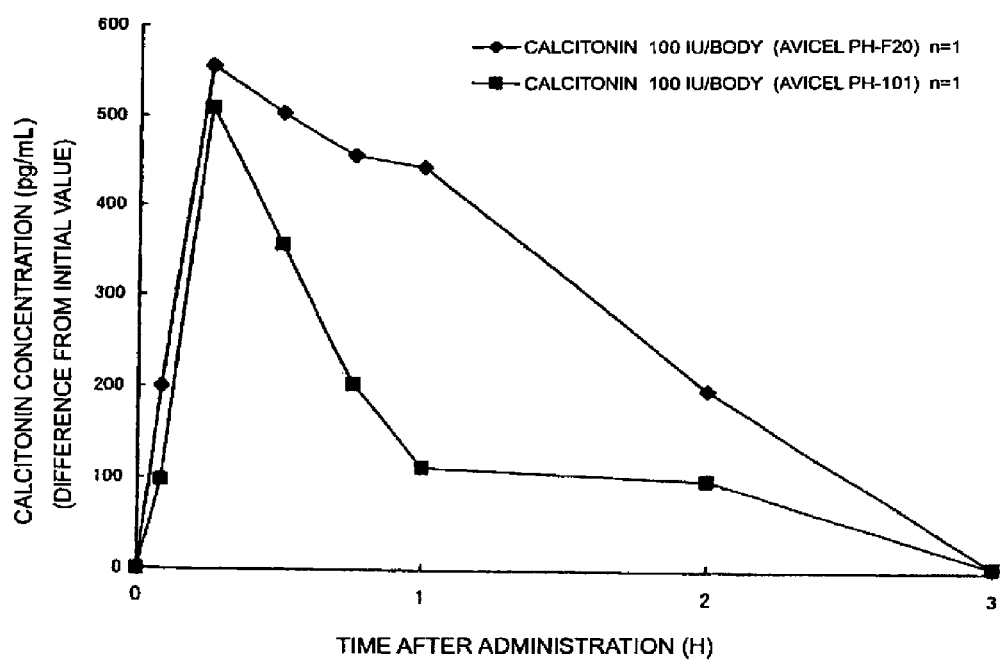
FIG. 7 is a graph showing changes in the blood pharmaceutical concentrations after intranasal administration of each salmon calcitonin-comprising composition to cynomolgus monkeys.
Figure 8:
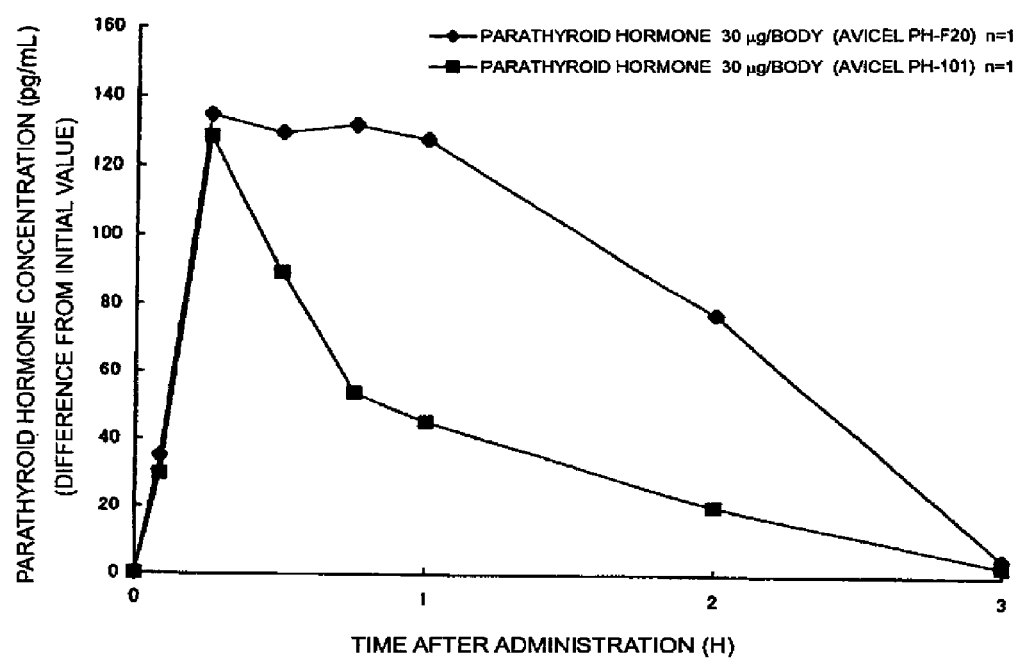
FIG. 8 is a graph showing changes in the blood pharmaceutical concentrations after intranasal administration of each parathyroid hormone-comprising composition to cynomolgus monkeys.

Time-course changes in the blood concentrations of glucagon, salmon calcitonin, and parathyroid hormone are shown in FIGS. 6, 7, and 8, respectively. Raw data for FIGS. 6, 7, and 8 are shown in Tables 15, 16, and 17.

TABLE 15

Administration of glucagon (Time-course changes in glucagon concentrations)

| Animal No. | Glucagon (pg/mL) (the initial value is subtracted) | | | | | | | |
|---|---|---|---|---|---|---|---|---|
| | 0 | 5 min | 15 min | 30 min | 45 min | 1 hr | 2 hr | 3 hr |
| Avicel PH-F20 1 | 0 | 49 | 358 | 400 | 396 | 350 | 150 | 10 |
| Avicel PH-101 1 | 0 | 35 | 347 | 303 | 250 | 99 | 55 | −5 |

TABLE 16

Administration of salmon calcitonin (Time-course changes in salmon calcitonin concentrations)

| Animal No. | Salmon calcitonin (pg/mL) (the initial value is subtracted) | | | | | | | |
|---|---|---|---|---|---|---|---|---|
| | 0 | 5 min | 15 min | 30 min | 45 min | 1 hr | 2 hr | 3 hr |
| Avicel PH-F20 1 | 0.00 | 200.31 | 555.23 | 504.01 | 456.21 | 443.86 | 198.11 | 4.53 |
| Avicel PH-101 1 | 0.00 | 97.22 | 509.56 | 356.64 | 203.77 | 112.39 | 99.19 | 4.76 |

TABLE 17

Administration of parathyroid hormone (Time-course changes in parathyroid hormone concentrations)

| Animal No. | Parathyroid hormone (pg/mL) (the initial value is subtracted) | | | | | | | |
|---|---|---|---|---|---|---|---|---|
| | 0 | 5 min | 15 min | 30 min | 45 min | 1 hr | 2 hr | 3 hr |
| Avicel PH-F20 1 | 0.00 | 34.9 | 134.6 | 129.6 | 131.9 | 127.8 | 77.3 | 5.1 |
| Avicel PH-101 1 | 0.00 | 29.6 | 128.4 | 89.3 | 53.8 | 45.3 | 20.3 | 2.9 |

The glucagon-, salmon calcitonin-, and parathyroid hormone-comprising compositions for nasal administration, respectively shown in FIGS. 6, 7, and 8, which use Avicel® PH-F20 as a carrier, have an absorbability clearly higher than those using Avicel® PH-101 as a carrier.

INDUSTRIAL APPLICABILITY

The present invention provides compositions for nasal administration which are capable of efficiently increasing the blood concentration of pharmaceuticals. Thus, compositions of the present invention can be utilized in the medical field including the pharmaceutical industry.

The invention claimed is:

1. A method of intranasally administering a physiologically active peptide or peptide-related compound, the method comprising:
intranasally administering a powdery pharmaceutical composition comprising:
the physiologically active peptide or peptide-related compound; and
a carrier,
wherein:
the physiologically active peptide or peptide-related compound has a molecular weight of 30,000 or less, and the carrier comprises crystalline cellulose particles, wherein 85 wt % or more of the crystalline cellulose particles are in a sieving particle diameter range of 20-60 µm, and wherein the crystalline cellulose particles have an average polymerization degree of about 20 to 250.

2. The method of claim 1, wherein the physiologically active peptide or peptide-related compound is selected from the group consisting of insulin, human growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, cyclosporine, and FK-506.

3. The method of claim 1, wherein the powdery pharmaceutical composition comprises insulin.

4. The method of claim 1, wherein the powdery pharmaceutical composition comprises human growth hormone.

5. The method of claim 1, wherein the powdery pharmaceutical composition comprises glucagon.

6. The method of claim 1, wherein the powdery pharmaceutical composition comprises glucagon-like peptide-1.

7. The method of claim 1, wherein the powdery pharmaceutical composition comprises calcitonin.

8. The method of claim 1, wherein the powdery pharmaceutical composition comprises parathyroid hormone.

9. The method of claim 1, wherein the powdery pharmaceutical composition comprises parathyroid hormone (1-34).

10. The method of claim 1, wherein the powdery pharmaceutical composition comprises luteinizing hormone-releasing hormone.

11. The method of claim 1, wherein the physiologically active peptide or peptide-related compound is in the form of a powder finer than the crystalline cellulose particles.

12. The method of claim 1, wherein the crystalline cellulose particles have a sieving particle diameter distribution of:
about 10 wt % or fewer particles with a diameter smaller than 25 µm;
about 20 to 60 wt % particles with a diameter of about 25 to 38 µm;
about 20 to 60 wt % particles with a diameter greater than 38 µm and smaller than 53 µm or equal to about 53 µm; and
the remaining particles having a diameter greater than 53 µm but up to 60 µm or less.

13. The method of claim 1, wherein the crystalline cellulose particles have an average polymerization degree of about 30 to 50.

14. The method of claim 1, wherein the crystalline cellulose particles have a bulk density of about 0.22 to 0.65 g/cm$^3$.

15. The method of claim 1, wherein the crystalline cellulose particles have a bulk density of about 0.22 to 0.40 g/cm$^3$.

16. The method of claim 1, wherein the crystalline cellulose particles have a bulk density of about 0.22 g/cm$^3$.

17. The method of claim 1, wherein the physiologically active peptide is intranasally administered.

18. The method of claim 1, wherein the physiologically active peptide-related compound is intranasally administered.

\* \* \* \* \*